US009440085B2

(12) United States Patent
Thakur

(10) Patent No.: US 9,440,085 B2
(45) Date of Patent: Sep. 13, 2016

(54) SYSTEM AND METHOD FOR ALERTING TO UNUSUAL/ATYPICAL PROGRAMMING CHANGES OF A MEDICAL DEVICE

(71) Applicant: Cardiac Pacemakers, Inc., St. Paul, MN (US)

(72) Inventor: Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/611,922

(22) Filed: Feb. 2, 2015

(65) Prior Publication Data

US 2015/0258343 A1  Sep. 17, 2015

Related U.S. Application Data

(60) Provisional application No. 61/953,991, filed on Mar. 17, 2014.

(51) Int. Cl.
*A61N 1/00* (2006.01)
*A61N 1/372* (2006.01)
*A61N 1/39* (2006.01)
*G06F 19/00* (2011.01)
*A61N 1/37* (2006.01)

(52) U.S. Cl.
CPC ....... *A61N 1/37247* (2013.01); *A61N 1/37258* (2013.01); *A61N 1/3925* (2013.01); *G06F 19/3406* (2013.01); *A61N 1/37* (2013.01)

(58) Field of Classification Search
CPC .............. A61N 1/37; A61N 1/37247; A61N 1/37258; A61N 1/3925; G06F 19/3406
See application file for complete search history.

(56) References Cited

U.S. PATENT DOCUMENTS

| 4,421,122 | A  | * | 12/1983 | Duffy ............................. 600/544 |
| 6,584,352 | B2 |   | 6/2003  | Combs et al. |
| 7,729,760 | B2 | * | 6/2010  | Patel et al. ......................... 607/2 |
| 7,978,062 | B2 |   | 7/2011  | LaLonde et al. |
| 8,373,556 | B2 |   | 2/2013  | LaLonde et al. |
| 8,395,498 | B2 |   | 3/2013  | Gaskill et al. |
| 8,515,547 | B2 |   | 8/2013  | Mass et al. |
| 2007/0150025 | A1 | * | 6/2007 | Dilorenzo et al. .............. 607/45 |

* cited by examiner

*Primary Examiner* — George Manuel
(74) *Attorney, Agent, or Firm* — Pauly, DeVries Smith & Deffner, LLC

(57) ABSTRACT

An apparatus comprises a communication circuit configured to communicate information with an ambulatory medical device, a user interface configured to receive a programmable parameter for the ambulatory medical device from a user, a memory to store a distribution of values for the programmable parameter, wherein the distribution is representative of values of the parameter programmed for a patient population, and a processor circuit configured to compare a received value of the programmable parameter to a distribution of programmed values for the programmable parameter and present results of the comparison to the user via a display of the user interface.

20 Claims, 7 Drawing Sheets

NEW MODE

| | AAIR | B OFF | DDD | DDDR | DDIR | VVI | VVIR |
|---|---|---|---|---|---|---|---|
| AAIR | - | 0 | 0 | 0 | 0 | 0 | 0 |
| B OFF | 0 | - | 0 | 0 | 0 | 0 | 1 |
| DDD | 0 | 2 | - | 43 | 0 | 1 | 1 |
| DDDR | 1 | 0 | 15 | - | 0 | 1 | 4 |
| DDIR | 0 | 0 | 0 | 0 | - | 0 | 1 |
| VVI | 0 | 0 | 1 | 1 | 0 | - | 1 |
| VVIR | 0 | 0 | 0 | 1 | 0 | 1 | - |

OLD MODE

NEW LRL

| OLD LRL | 95 | 90 | 85 | 80 | 75 | 70 | 65 | 60 | 55 | 50 | 45 | 40 | 35 |
|---|---|---|---|---|---|---|---|---|---|---|---|---|---|
| 95 | - | 0 | 0 | 1 | 0 | 0 | 0 | 0 | 0 | 0 | 0 | 0 | 0 |
| 90 | 0 | - | 0 | 0 | 0 | 0 | 0 | 0 | 0 | 0 | 0 | 0 | 0 |
| 85 | 0 | 0 | - | 0 | 0 | 0 | 0 | 0 | 0 | 0 | 0 | 0 | 0 |
| 80 | 0 | 0 | 0 | - | 1 | 2 | 0 | 0 | 0 | 1 | 0 | 0 | 0 |
| 75 | 0 | 0 | 0 | 1 | - | 1 | 0 | 0 | 0 | 0 | 0 | 0 | 0 |
| 70 | 0 | 0 | 0 | 2 | 2 | - | 1 | 1 | 0 | 1 | 0 | 0 | 0 |
| 65 | 0 | 0 | 0 | 0 | 0 | 1 | - | 0 | 0 | 0 | 0 | 1 | 0 |
| 60 | 0 | 0 | 1^ | 3 | 0 | 4 | 1 | - | 0 | 0 | 6 | 1 | 0 |
| 55 | 1* | 0 | 0 | 0 | 0 | 0 | 0 | 0 | - | 0 | 0 | 0 | 0 |
| 50 | 0 | 0 | 0 | 0 | 0 | 3 | 0 | 3 | 0 | - | 0 | 1 | 1 |
| 45 | 0 | 0 | 0 | 0 | 0 | 0 | 1 | 7 | 0 | 0 | - | 0 | 0 |
| 40 | 0 | 0 | 0 | 0 | 0 | 1^ | 0 | 1 | 0 | 0 | 0 | - | 0 |
| 35 | 0 | 0 | 0 | 0 | 0 | 0 | 0 | 0 | 0 | 1 | 0 | 0 | - |

*FIG. 7*

SYSTEM AND METHOD FOR ALERTING TO UNUSUAL/ATYPICAL PROGRAMMING CHANGES OF A MEDICAL DEVICE

CLAIM OF PRIORITY

This application claims the benefit of priority under 35 U.S.C. §119(e) of U.S. Provisional Patent Application Ser. No. 61/953,991, filed on Mar. 17, 2014, which is herein incorporated by reference in its entirety.

BACKGROUND

Ambulatory medical devices include implantable medical devices (IMDs) and wearable medical devices. Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and may include electrodes that are able to sense cardiac signals without being in direct contact with the patient's heart. Other examples of IMDs include implantable diagnostic devices, implantable drug delivery systems, or implantable devices with neural stimulation capability.

Some examples of wearable medical devices include wearable cardioverter defibrillators (WCDs) and wearable diagnostic devices (e.g., an ambulatory monitoring vest). WCDs can be monitoring devices that include surface electrodes. The surface electrodes may be arranged to provide one or both of monitoring to provide surface electrocardiograms (ECGs) and delivery of cardioverter and defibrillator shock therapy. A wearable medical device can also include a monitoring patch worn by the patient such as an adherable patch or a patch included with an article of clothing worn by the patient.

Therapy provided by ambulatory medical devices is typically optimized by a caregiver, such as by programming different operating parameters of the medical device for example. Manufacturers of such devices continue to improve and add functionality to the devices, which can make them complicated to program and optimize to the needs of a particular patient. The inventor has recognized a need for improved optimization of device-based therapy.

Overview

As explained previously herein, therapy provided by ambulatory medical devices is typically optimized by a caregiver in a clinical setting. A specific recipe or rule for mapping device parameters to an individual patient does not exist. Identifying the optimal programming parameters for a patient can be partly science and partly art and some amount of trial-and-error can be involved in the approach a given physician uses in tailoring a device to an individual patient. Sometimes physicians may program one or more parameters to be outliers having values that are not normally used by physicians. This programming of outlier parameters may be useful to improve hemodynamic function of the patient or may adversely affect the patient. The present subject matter can help a physician determine optimal settings for the patient.

An apparatus example of the present subject matter includes a communication circuit configured to communicate information with an ambulatory medical device, a user interface configured to receive a programmable parameter for the ambulatory medical device from a user, a memory to store a distribution of values for the programmable parameter, wherein the distribution is representative of values of the parameter programmed for a patient population, and a processor circuit configured to compare a received value of the programmable parameter to a distribution of programmed values for the programmable parameter and present results of the comparison to the user via a display of the user interface.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 4-7 show examples of presenting feedback of a programming change to a user.

DETAILED DESCRIPTION

Figure 1:
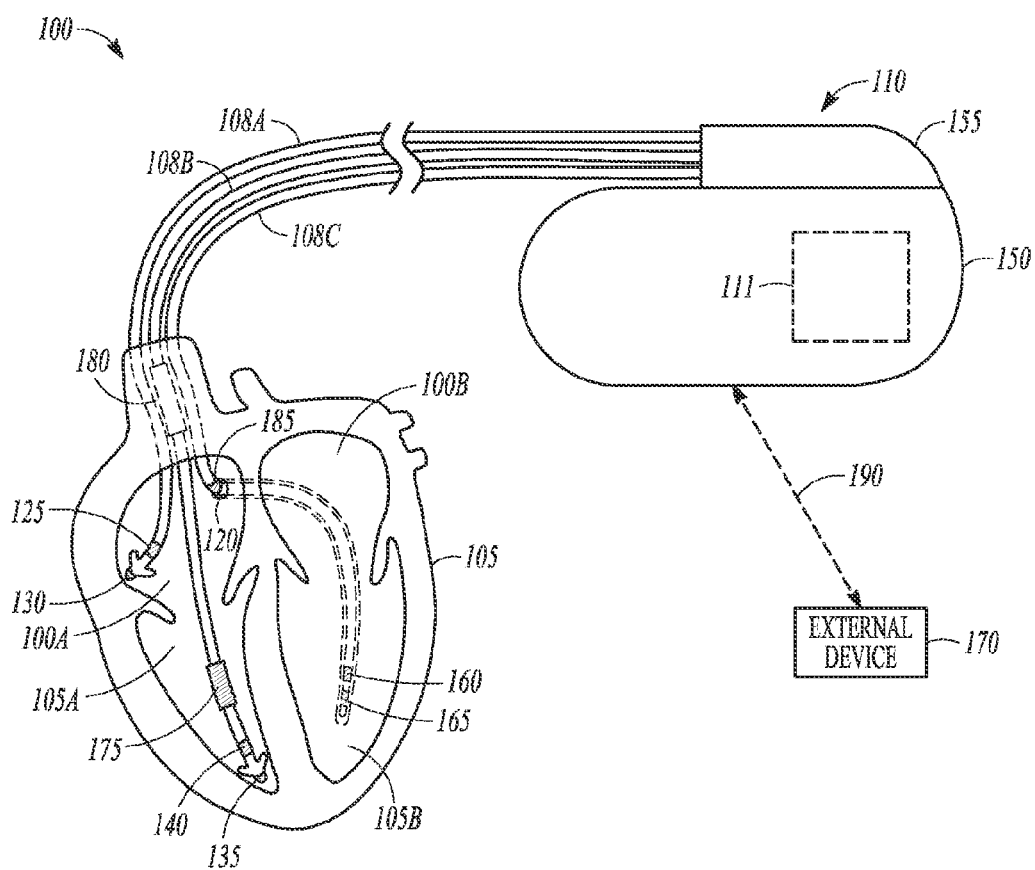
FIG. 1 illustrates portions of an example of a medical device system that includes an ambulatory medical device.

FIG. 1 is an illustration of portions of an example of a medical device system 100 that includes an ambulatory medical device that is an IMD 110. Examples of MID 110 include, without limitation, a pacer, a defibrillator, a CRT device, or a combination of such devices. The system 100 also typically includes an external device 170 that may be an IMD programmer or other external device to communicate wireless signals 190 with the IMD 110, such as by using radio frequency (RF) or other telemetry signals.

The IMD 110 is shown coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 120. Although only two electrodes are shown in the example of the Figure, lead 108C may include three electrodes, four electrodes, or any number of electrodes as desired.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC), In some examples, high-energy shock therapy is delivered from the first or RV coil 175 to the second or SVC coil 180. In some examples, the SVC coil 180 is electrically tied to an electrode 111 formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150, In some examples, the coil electrodes 175, 180 are used in combination with other electrodes for sensing signals.

Figure 2:
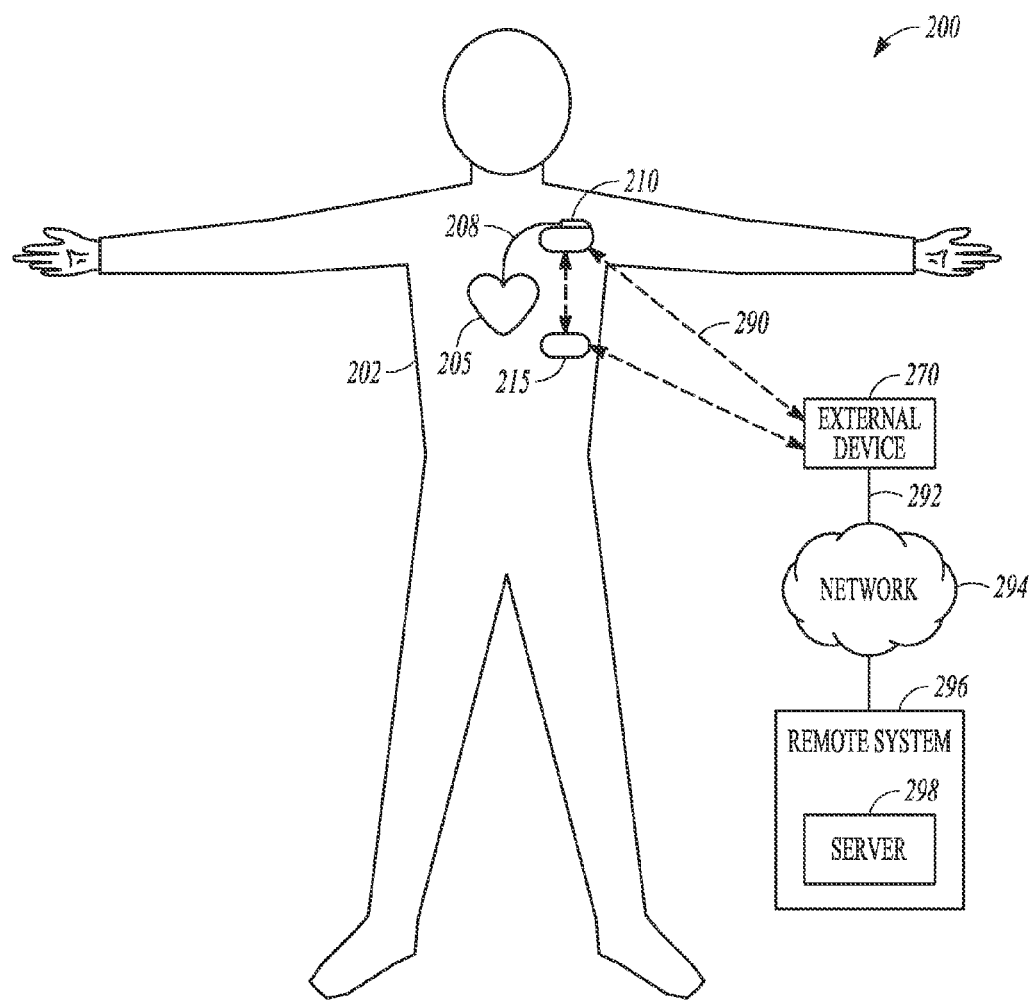
FIG. 2 illustrates portions of an example of a medical device system that includes one or more ambulatory medical devices.

FIG. 2 is an illustration of portions of an example of a medical device system 200 that includes one or more ambulatory medical devices, The one or more ambulatory medical devices can include an IMD 210 and a wearable medical device 215. The IMD 210 may provide a therapy to a patient 202. The wearable medical device 215 may be a patch device that monitors one or more physiological parameters of the subject. The wearable medical device 205 may be incorporated into an article of clothing or may be temporarily adherable to the subject's skin.

The system can include an external device 270 that communicates with a remote system 296 via a network 294. The network 294 can be a communication network such as a phone network or a computer network (e.g., the internee). In some examples, the external device 270 includes a repeater and communicates via the network using a link 292 that may be wired or wireless. In some examples, the remote system 296 provides patient management functions and may include one or more servers 298 to perform the functions. In certain examples, medical device system 200 includes both the wearable medical device 215 and the IMD 210, and the wearable medical device 215 communicates wirelessly with the MID 210.

As explained previously herein, adjusting the settings of an ambulatory medical device to optimize device-based therapy can benefit the subject by improving the subject's hemodynamic status. Yet sometimes physicians may program one or more parameters to outlier values not normally used by physicians. Feedback provided to the physician that is based on how the selected or programmed parameter change compares to values of the parameter historically programmed for a patient population may help the physician identify outlier parameter changes from normal parameter changes. This can aid the physician to avoid unintended consequences in determining optimized settings for the individual patient.

Figure 3:
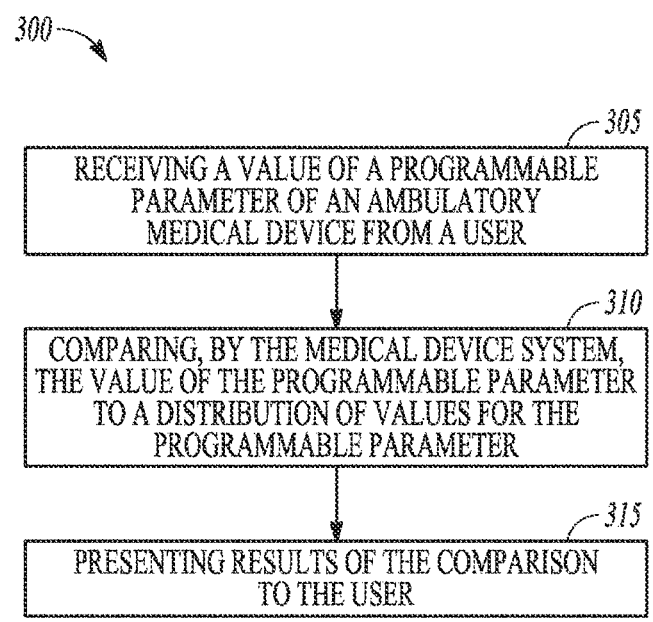
FIG. 3 shows an example of a method of operating a medical device system.

FIG. 3 shows an example of a method 300 of operating a medical device system. The medical device system can include some or all of the components of the system shown in FIG. 2. The method 300 may be processor-implemented and may be performed by one or more processors of the medical device system executing instructions to perform the functions described.

At 305, a value of a programmable parameter of an ambulatory medical device is received from a user. The value of the programmable parameter can be received into a programming device for the ambulatory medical device. In some examples, the value of the programmable parameter is uploaded from the ambulatory medical device to a server.

At 310, the value of the programmable parameter is compared to a distribution of values for the programmable parameter. The distribution can be representative of values of the parameter programmed for a patient population. For example, a physician may have a patient with heart failure (HF) who is prescribed a device to provide CRT. Because the patient has HF, the patient may experience shortness of breath. To improve the shortness of breath, the physician may attempt to program the CRT device into AAI mode. (AAI mode refers to the NASPE/BPEG (North American Society of Pacing and Electrophysiology, and British Pacing and Electrophysiology Group) code fur atrial sensing and pacing.) However, such a change is counter-intuitive given the importance of bi-ventricular (BiV) pacing. If the reprogramming of the pacemaker mode is uploaded to a server, the server can perform a comparison of the change in value of the mode to the distribution of programming modes. The distribution can be obtained by pooling data from most or all of the patients that have similar characteristics to the patient under consideration. Such characteristics may include disease history, co-morbid conditions, common demographic variables such as age, sex, etc., and may include clinical metrics.

Figures 4, 5:
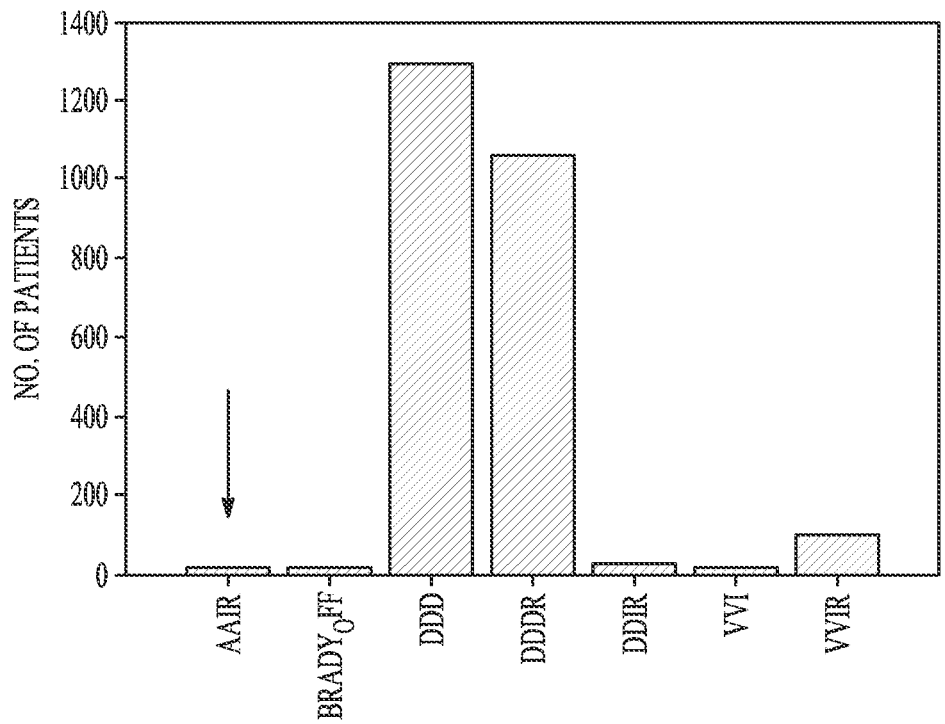

At block 315, results of the comparison can be presented to the user. This can provide feedback on how atypical such a mode change would be. FIGS. 4 and 5 show some examples of how the comparison may be presented to a user. FIG. 4 shows the distribution on a bar graph display and indicates (e.g., with an arrow) the mode change in comparison to historical changes of the pacing mode. FIG. 5 shows the mode change in a chart format highlighting (e.g., by a circle) or otherwise indicating the change in mode made by physician or desired to be made by the physician.

In another example, a physician may have a patient who was prescribed a pacemaker but the patient is not feeling well or may be experiencing syncope. The physician may desire to increase the lower rate limit (LRL) of the pacemaker in order to improve the patient's hemodynamic function. The LRL sets the interval at which an electrical pulse is applied to the myocardium to initiate cardiac depolarization and ultimately cardiac contraction. However, the change to the LRL increases the heart rate of the patient, but may not affect the systolic interval during which the ventricles of the heart contract to eject blood. The change in LRL may have the unintended effect of shortening the diastolic interval (during which the ventricles of the heart fill with blood) disproportionately as compared to the systolic interval with the result that hemodynamic function of the patient is worsened because the ventricles do sufficiently fill before ejection.

Figure 6:
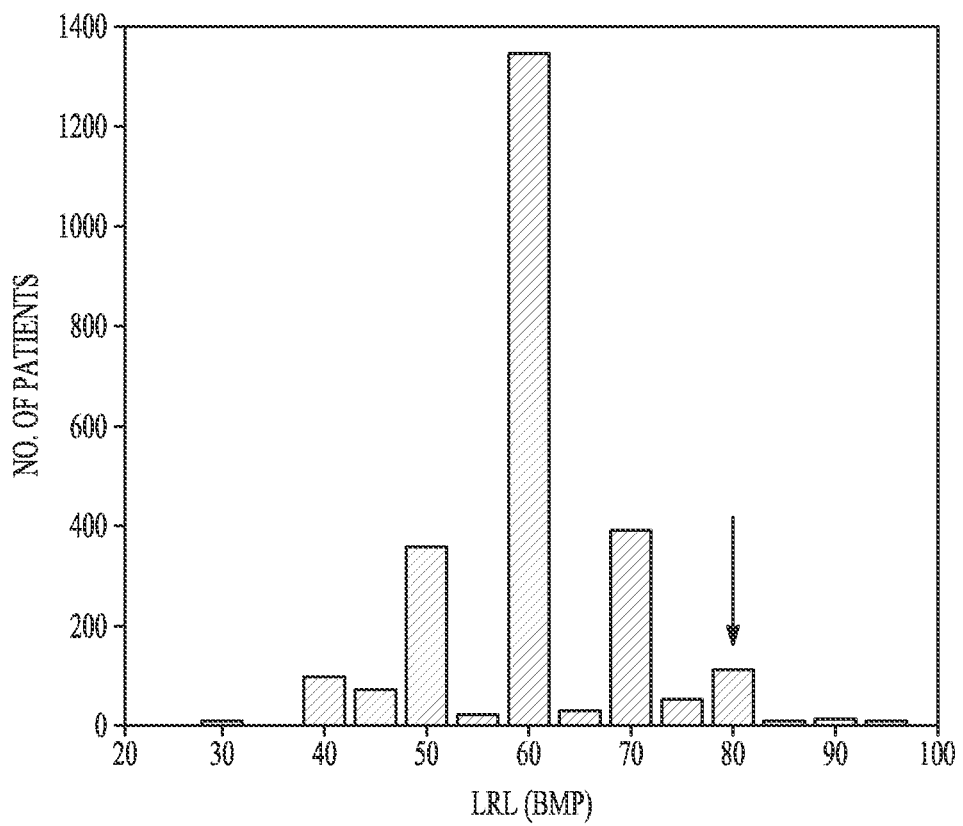

If the reprogramming of the LRL is entered into a device programmer, the programmer can perform a comparison of the change in value of the LRL to the distribution of programmed changes to the LRL and present results of the comparison to the user. FIGS. 6 and 7 some examples of how the comparison may be presented to a user.

Figure 8:
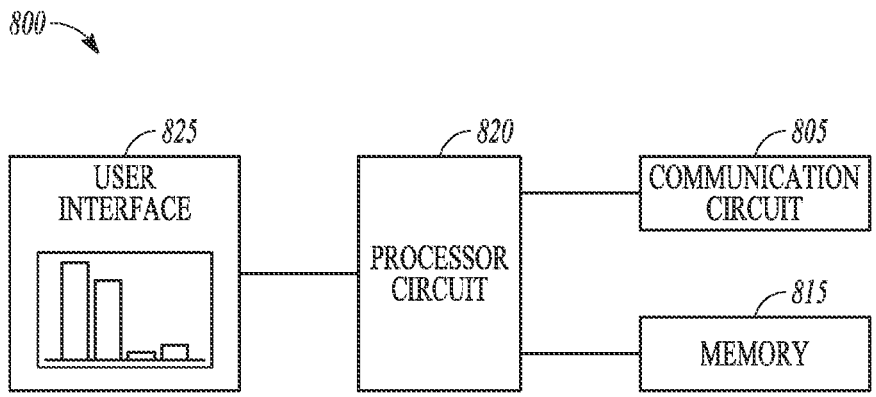
FIG. 8 shows a block diagram of portions of an example of a medical device.

FIG. 8 shows a block diagram of an example of portions of an example of a medical device 800. The medical device 800 includes a communication circuit 805, a user interface 825, a memory 815, and a processor circuit 820. The communication circuit 805 communicates information with an ambulatory medical device. The communication can be wireless and can be implemented using one or both of mutual inductance telemetry or longer range radio frequency (RF) telemetry.

The user interface 825 can include one or more of a display, a touch screen display, a keyboard, a keypad, a computer mouse. The user interface 825 receives a programmable parameter for the ambulatory medical device from a user. The programmable parameter maybe programmed into the ambulatory medical upon being received or can be programmed after a confirmation is entered via the user interface. The memory 815 can be integral to or separate from the processor circuit 820. The memory stores a distribution of values for the programmable parameter. The distribution can be representative of values of the parameter programmed for a patient population. The patient population may be a patient population with symptoms or disease similar to the patient using the device being programmed. The patient population may be a patient population with similar age and gender of the patient. The patient population may be a patient population with a device of the same type (e.g., same model) as the device being programmed.

The processor circuit 820 can include a microprocessor or application specific integrated circuit (ASIC). The processor circuit 820 can be configured to perform the functions described using one or more of hardware and executable instructions included in one or more of software and firmware. The processor circuit 820 compares a received value of the programmable parameter to the distribution of programmed values for the programmable parameter and present results of the comparison to the user via the display of the user interface 825.

In some examples, the processor circuit 820 presents an alert according to the result of the comparison with the distribution and communicates the received value of the programmable parameter to the ambulatory medical device upon receiving a confirmation of the value from the user via the user interface 825. In certain examples, the alert can be a highlight (e.g. a highlight in yellow) on the display. In certain examples the alert can be an indication such as an arrow or circle such as in the example of FIGS. 4-7. In certain examples, the alert can include an audible tone or can include tactile feedback in combination with a displayed alert. In certain examples, the alert is presented when the value of the change is programmed less than a specified percentage of the historical changes to the parameter.

In certain examples, the user interface includes a display and wherein the processor circuit is configured to present the received value of the programmable parameter in context with the distribution of programmed values for the programmable parameter. For instance, as shown in FIGS. 4-7 the value of the parameter is shown in context with other values programmed for the parameter. In certain examples, the value of the parameter is displayed in relation to a normalization curve for values of the parameter in the population distribution.

Because the distribution resides in memory it may be desirable to recurrently update stored distribution or distributions of parameter values. In some examples, the processor circuit 820 recurrently receives a distribution of values for the programmable parameter either wirelessly or through a wired communication port (not shown) and updates the stored distribution of values for the programmable parameter. In certain examples, the processor circuit 820 recurrently receives a distribution of values for the programmable parameter according to at least one of a model number or model type of the ambulatory medical device.

Figure 9:
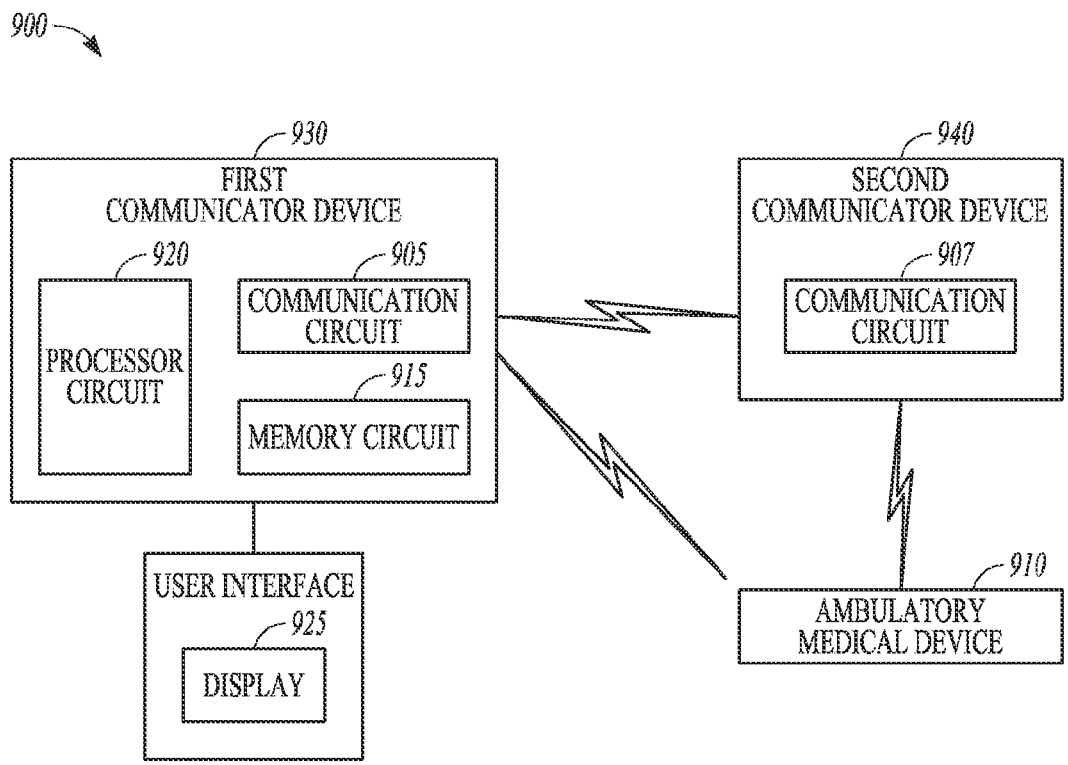
FIG. 9 shows a block diagram of portions of an example of a medical device system.

FIG. 9 shows a block diagram of portions of an example of a medical device system 900. The system includes a first communicator device. The first communicator device 930 includes a communication circuit 905 and a processor circuit 920. The communication circuit 905 communicates information associated with an ambulatory medical device 910. The processor circuit 920 determines that a current value of a programmable parameter of the ambulatory medical is different from a previous value of the programmable parameter and compares the current value of the programmable parameter to a distribution of programmed values for the programmable parameter. The distribution is representative of values of the parameter programmed for a patient population. The processor circuit 920 presents results of the comparison to a user such as by display 925.

According to some examples, the medical device system 900 can include a second communicator device 940 having a communication circuit 907 that communicates programmable information with the ambulatory medical device 910, and communicates programmable information for the ambulatory medical device 910 with the first communicator device 930. The first communicator device 930 can communicate programmable information with the ambulatory medical device 910 via the second communicator device 940.

The communication circuit 907 of the second communicator device 940 can be configured for local communication with the ambulatory medical device 910. For instance, the second communicator device can be a home communicator device for the ambulatory medical device. The second communicator device and the ambulatory medical device may communicate wirelessly using long range or far-field RE telemetry or by using near-field telemetry such as mutual inductance telemetry. In certain examples, the ambulatory medical device is an implantable cardiac function management device.

The communication circuit 905 of the first communicator device 930 can be configured for remote communication with the second communicator device. For instance, the first communicator device can include a remote server. In certain examples, the first and second communicator devices communicate wirelessly using long range RE telemetry. In certain examples the first communicator device and the second communicator device communicate via a computer network or a cellular telephone network.

The first communicator device 930 can include a memory circuit 915, integral to or incorporated into the processor circuit 920, to store one or more distributions for the programmed values for the programmable parameter. The processor circuit 920 may determine a characteristic of a patient for the ambulatory medical device and compares the value of the programmable parameter to a distribution for a patient population having a similar characteristic. In certain examples, the characteristic is an indication of one or more symptoms or disease of the patient. In certain examples, the characteristic is an indication of a comorbidity of the patient, such as a patient with cardiac disease who also has diabetes.

In certain examples, the characteristic is determined using one or both of the model type or the model number of the ambulatory medical device and the processor circuit 920 identifies the distribution for comparison of the current value of the programmable parameter using at least one of the model type or model number of the ambulatory medical device. The display 925 may be used to present the value of the programmable parameter in context with the distribution of programmed values for the programmable parameter using the display.

The several examples of methods, systems and devices described herein can provide helpful feedback to a physician on how current programming changes or proposed changes compare with changes made historically for similar patients or for similar devices. The programming changes can be presented in context with the historical changes to help show the degree to which the change is in line with normal programming. Notification of atypical programming changes can result in improved optimization of the devices.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A hut not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of operating a medical device system, the method comprising:
   receiving a value of a programmable parameter of an ambulatory cardiac rhythm device from a user;
   comparing, by the medical device system, the value of the programmable parameter to a distribution of values for the programmable parameter, wherein the distribution is representative of values of the parameter programmed for a patient population; and
   presenting results of the comparison to the user;
   wherein the programmable parameter is a mode in which the cardiac rhythm device operates or a lower rate limit for the cardiac rhythm device;
   wherein presenting the results of the comparison to the user includes identifying a number of occurrences of the value of the parameter programmed in the patient population.

2. The method of claim 1,
wherein receiving the value of a programmable parameter includes receiving a value of a programmable parameter into a programming device for the ambulatory cardiac rhythm device;
wherein comparing the value of the programmable parameter to a distribution includes comparing the value of the programmable parameter to a distribution of programmed values for the programmable parameter stored in the programming device; and
wherein presenting the result of the comparison includes presenting the results of the comparison to the user using a display of the programming device.

3. The method of claim 2, including recurrently updating the distribution of values for the programmable parameter stored in the programming device.

4. The method of claim 2, wherein presenting the result of the comparison includes presenting an alert according to the result of the comparison to the distribution and changing the value of the programmable parameter upon receiving a confirmation from the user at the programming device.

5. The method of claim 1,
wherein receiving the value of a programmable parameter includes uploading the value of the programmable parameter from the ambulatory cardiac rhythm device to a server;
wherein comparing the value of the programmable parameter to a distribution includes comparing the value of the programmable parameter to a distribution of values for the programmable parameter stored in the server; and
wherein presenting the result of the comparison includes communicating an indication of the result of the comparison to a second device for presentation to the user.

6. The method of claim 5, wherein receiving the value of a programmable parameter includes uploading the value of the programmable parameter using a communicator device located locally to the ambulatory cardiac rhythm device and communicating the value of the programmable parameter to a server located remotely from the ambulatory cardiac rhythm device.

7. The method of claim 1, wherein comparing the value of the programmable parameter to a distribution includes matching a characteristic of a patient for the ambulatory cardiac rhythm device to a distribution for a patient population having a similar characteristic.

8. The method of claim 1, wherein presenting the result of the comparison includes presenting the value of the programmable parameter in context with the distribution of programmed values for the programmable parameter.

9. An apparatus comprising:
a communication circuit configured to communicate information with an ambulatory cardiac rhythm device;
a user interface configured to receive a programmable parameter for the ambulatory cardiac rhythm device from a user;
a memory to store a distribution of values for the programmable parameter, wherein the distribution is representative of values of the parameter programmed for a patient population; and
a processor circuit configured to compare a received value of the programmable parameter to a distribution of programmed values for the programmable parameter and present results of the comparison to the user via a display of the user interface;
wherein the results of the comparison includes identification of a number of occurrences of the value of the parameter programmed in the patient population;
wherein the programmable parameter is a mode in which the cardiac rhythm device operates or a lower rate limit for the cardiac rhythm device.

10. The apparatus of claim 9, wherein the processor circuit is configured to present an alert according to the result of the comparison to the distribution and communicate the received value of the programmable parameter to the ambulatory cardiac rhythm device upon receiving a confirmation of the value via the user interface.

11. The apparatus of claim 10, wherein the processor circuit is configured to recurrently receive a distribution of values for the programmable parameter according to at least one of a model number or model type of the ambulatory cardiac rhythm device.

12. The apparatus of claim 9, wherein the processor circuit is configured to recurrently receive a distribution of values for the programmable parameter and update the stored distribution of values for the programmable parameter.

13. The apparatus of claim 9, wherein the user interface includes a display and wherein the processor circuit is configured to present the received value of the programmable parameter in context with the distribution of programmed values for the programmable parameter.

14. A medical device system comprising a first communicator device including:
a communication circuit configured to communicate information associated with an ambulatory cardiac rhythm device; and
a processor circuit configured to:
determine that a current value of a programmable parameter of the ambulatory cardiac rhythm device is different from a previous value of the programmable parameter;
compare the change in value of the programmable parameter to a distribution of changes in values for the programmable parameter, wherein the distribution is representative of changes in values of the parameter programmed for a patient population; and
present results of the comparison to a user, wherein the results of the comparison includes identifying a number of occurrences of the change in value of the parameter programmed in the patient population;
wherein the programmable parameter is a mode in which the cardiac rhythm device operates or a lower rate limit for the cardiac rhythm device.

15. The system of claim 14, including:
a second communicator device including a communication circuit configured to communicate programmable information with the ambulatory cardiac rhythm device and to communicate programmable information for the ambulatory cardiac rhythm device with the first communicator device,
wherein the first communicator device is configured to communicate information with the ambulatory cardiac rhythm device via the second communicator device,
wherein the communication circuit of the second communicator device is configured for local communication with the ambulatory cardiac rhythm device, and
wherein the communication circuit of the first communicator device is configured for remote communication with the second communicator device.

16. The system of claim 15, wherein the second communicator device includes a home communicator device for the ambulatory cardiac rhythm device and the first communicator device includes a server.

17. The system of claim 14, wherein the communication circuit of the second communicator device is configured to communicate information with an implantable cardiac function management device.

18. The system of claim 14, wherein the first communicator device includes a memory circuit configured to store one or more distributions for the programmed values for the programmable parameter, and wherein the processor circuit is configured to determine a characteristic of a patient for the ambulatory cardiac rhythm device and to compare the value of the programmable parameter to a distribution for a patient population having a similar characteristic.

19. The system of claim 18, wherein the processor circuit is configured to identify a distribution for comparison of the current value of the programmable parameter using at least one of a model type or model number of the ambulatory cardiac rhythm device.

20. The system of claim 14, including a display, wherein the first communicator device is configured to present the value of the programmable parameter in context with the distribution of programmed values for the programmable parameter using the display.

* * * * *